March 14, 1961 J. A. YOUDATH Plant Pat. 2,034
DIANTHUS PLANT
Filed Jan. 18, 1960
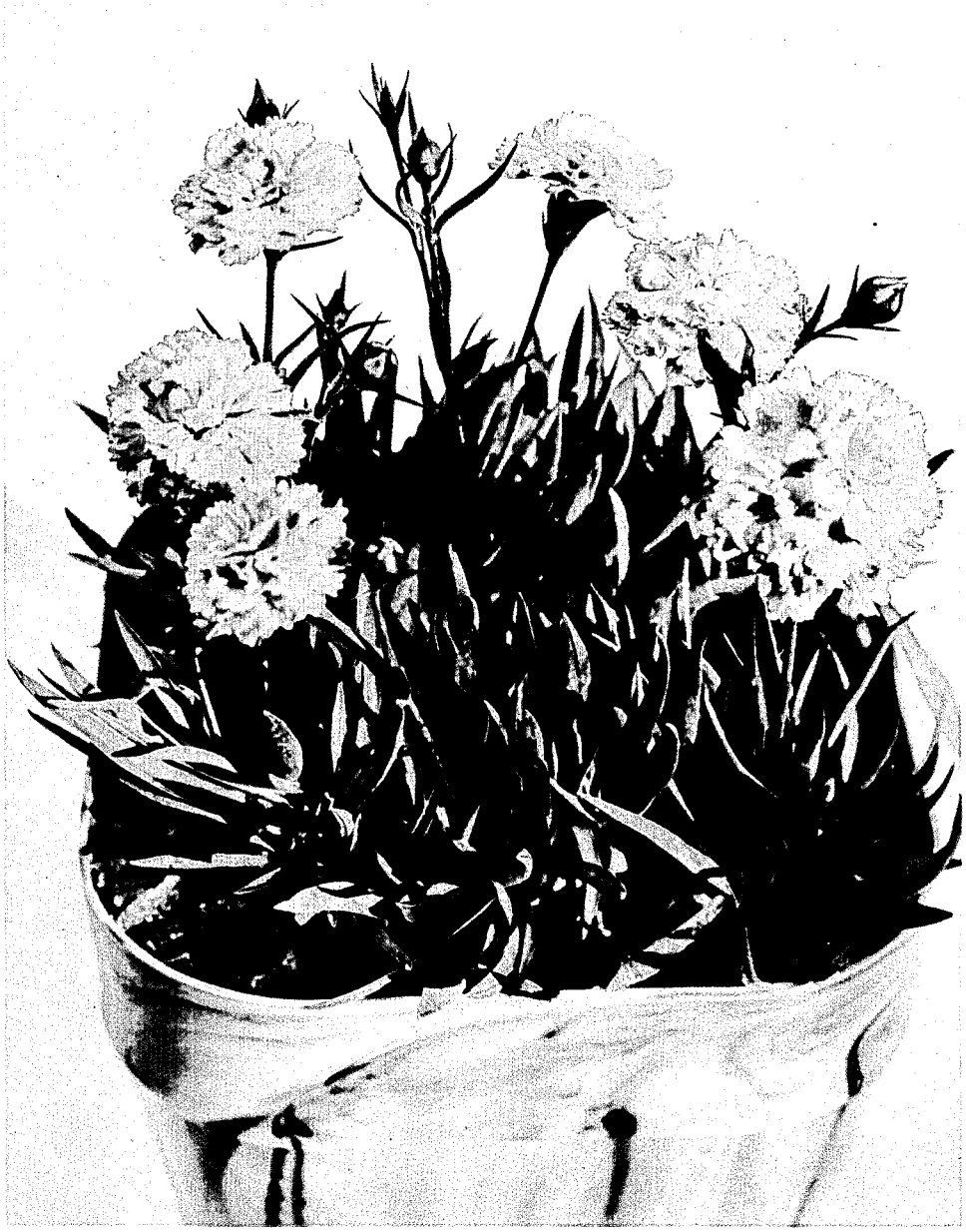
INVENTOR:
JOHN A. YOUDATH
BY Herbert E. Fidder
AGENT United States Patent Office Plant Pat. 2,034
Patented Mar. 14, 1961

2,034

DIANTHUS PLANT

John A. Youdath, Beaumont, Calif., assignor to Jacob Mittleider, Loma Linda, Calif.

Filed Jan. 18, 1960, Ser. No. 3,216

1 Claim. (Cl. 47—60)

The present invention relates to a new and distinct variety of dianthus plant, which is characterized particularly by a low growing, compact, densely tufted plant bearing numerous large, very double flowers of a distinctive shade of magenta color and having a spicy, carnation-like fragrance.

The present variety is a cross produced in the experimental section of my nursery at Beaumont, California; the cross being made by pollen from an unnamed carnation seedling with a deep rose flower, on a Ruby Gem (unpatented) dianthus of the alpine rock garden variety.

The new variety of plant produced by this cross has a very double flower of a distinctive magenta color, ranging from a relatively light magenta to a considerably darker shade of magenta, depending upon the prevailing temperature. The flowers are extremely fragrant, and the plant makes an exceedingly attractive ground cover, border planting, or potted plant. The original reproduction of the variety by cuttings was carried out in the experimental section of my nursery at Beaumont, California.

The plant grows best in well drained, loamy soil, but is not critical as to the pH of the soil. Best blooming is obtained when the plants are grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Beaumont and Loma Linda, California, with color terminology and identifications in accordance with "A Dictionary of Color" by Maerz and Paul:

Plant:

*Form.*—Compact, growing to a height of three to five inches.

*Growing habit.*—Densely tufted.

*Blooming habit.*—Floriferous, flowering evenly over the entire plant, with blossoms ranging in number from 3 or 4 on one year old plants grown in three inch pots, up to 20 or 30 on two year old plants grown in gallon-size containers.

*Blooming season.*—Perpetual in the temperate climate of southern California, although the plant will bloom down to temperatures below freezing. Maximum bloom in southern California occurs from May to August, while minimum bloom occurs from November to February.

Foliage:

*Size.*—Maximum size of mature leaves on thrifty young plants is approximately four inches in length, by five-eighths inch in width.

*Quantity.*—Abundant.

*Shape.*—Lanceolate, or grass-like.

*Color.*—Growing under good conditions, the color of mature leaves ranges from Alfalfa, Plate 22–C–12 to Alpine, Plate 31–C–9, with young leaves somewhat lighter.

*Texture.*—Glaucous.

Flower:

*Size.*—The maximum size is about one and one-quarter inches across by one-half inch high.

*Borne.*—At the end of the stem.

*Stem.*—Stiff and upright.

*Petalage.*—Very double.

*Color.*—At the peak of the flowering season in late spring, the color is a light magenta, Plate 41–L–5. In cold weather, the color is a deeper shade of magenta, Plate 42–L–7.

*Petals.*—Firm in texture, of obovate form with regularly crenate margins. The size of the individual petals is approximately one-half inch in length by three-eighths inch in width.

*Fragrance.*—Spicy, carnation-like. Somewhat similar to Dianthus Old Spice (Plant Platent No. 499).

*Calyx.*—Spreading at the tips, with acuminate teeth, and approximately one-half inch long.

Compared to other well known dianthus plants, this plant has a distinctive low-growing, bushy, compact, densely tufted form, usually not exceeding three to five inches in height, with extremely fragrant, very double flowers, of magenta color and spicy, carnation-like fragrance.

I claim:

A new and distinct variety of dianthus plant, substantially as shown and described herein, characterized particularly by its floriferous blooming habit, low-growing, compact, densely turfted plant form, usually not exceeding three to five inches in height, and bearing many very double flowers of magenta color ranging from light to medium, depending upon the prevailing temperatures, said flowers having a spicy, carnation-like fragrance that is somewhat similar to Dianthus Old Spice (Plant Patent No. 499).

No references cited.